United States Patent [19]

Hazar

[11] Patent Number: 4,470,815

[45] Date of Patent: Sep. 11, 1984

[54] METHOD OF MAKING CUSTOM DENTURES

[75] Inventor: Mitchell M. Hazar, Scottsdale, Ariz.

[73] Assignee: Hazco Development, Inc., Tempe, Ariz.

[21] Appl. No.: 476,233

[22] Filed: Mar. 17, 1983

[51] Int. Cl.³ .............................................. A61C 13/22
[52] U.S. Cl. .................................. 433/171; 433/213; 264/18
[58] Field of Search ................. 433/171, 34, 167, 213, 433/214; 264/16, 17, 18

[56] References Cited

U.S. PATENT DOCUMENTS

| | | | |
|---|---|---|---|
| 1,729,461 | 9/1929 | Thayer | 433/196 |
| 2,985,961 | 5/1961 | Schwartz | 433/213 |
| 3,335,495 | 8/1967 | Wichner | 433/171 |
| 3,464,111 | 9/1969 | Gillard | 32/2 |
| 3,567,806 | 3/1971 | Dyal | 433/171 |
| 3,644,996 | 2/1972 | Weinkle | 433/171 |
| 3,667,123 | 6/1972 | Huey | 32/2 |
| 3,783,514 | 1/1974 | Kersten | 433/171 |
| 3,839,796 | 10/1974 | Hazar | 32/2 |
| 3,846,911 | 11/1974 | Wichner | 433/171 |
| 4,017,971 | 4/1977 | Hazar | 32/2 |
| 4,019,253 | 4/1977 | Hazar | 32/19 |
| 4,097,992 | 7/1978 | Hazar | 433/171 |
| 4,133,110 | 1/1979 | Bernstein et al. | 433/213 |
| 4,337,042 | 6/1982 | Nostitz | 433/171 |
| 4,370,133 | 1/1983 | Stempel | 433/171 |

Primary Examiner—John J. Wilson
Attorney, Agent, or Firm—Don J. Flickinger

[57] ABSTRACT

A method of making custom dentures from an uncured resin module wherein the module, molded to standard dimensions and including sockets for artificial teeth, is cooled to a low temperature to impart rigidity and prevent curing. The module with teeth in place is later conformed to a heated cast representation of the patient's oral cavity and then itself heated to cure the module thereby providing a custom denture.

17 Claims, 17 Drawing Figures

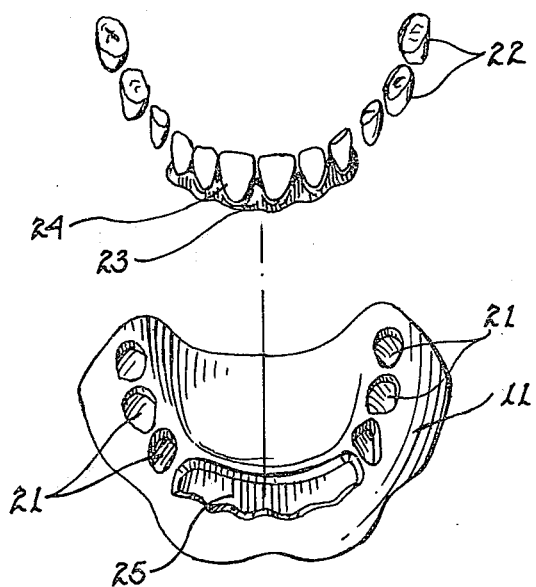
fig 7
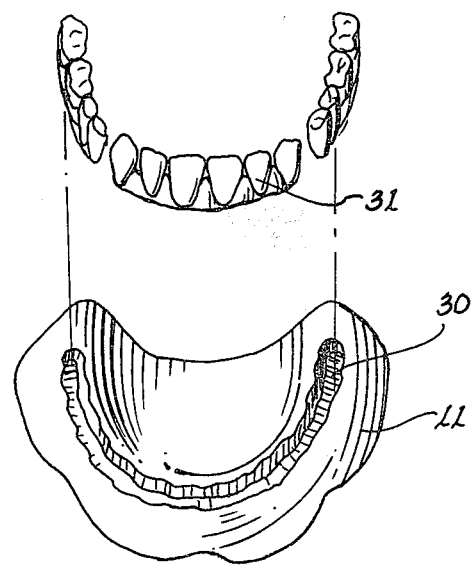
fig.8
fig.9
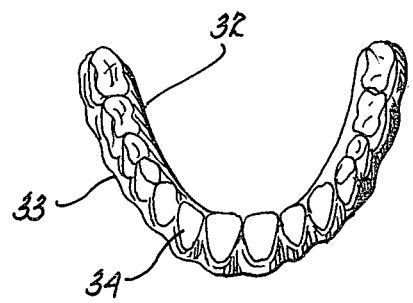
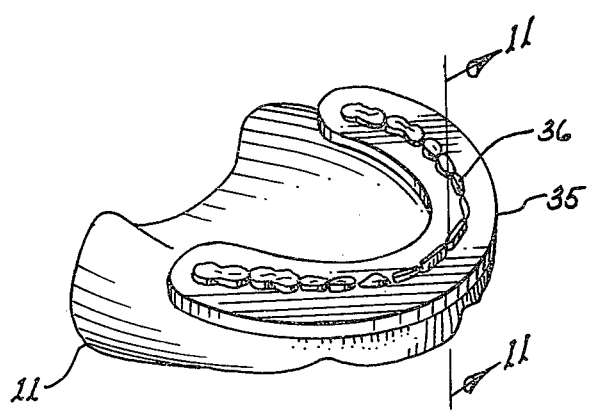
fig. 10
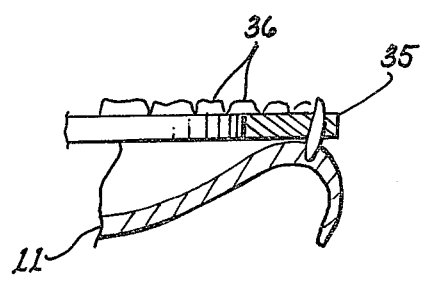
fig. 11

METHOD OF MAKING CUSTOM DENTURES

BACKGROUND OF THE INVENTION

This invention relates to a method for the formation and manufacture of custom dentures from synthetic materials and includes a novel dental module for use therein.

The increasing longevity of individual life spans throughout much of the world accompanied by a heightened awareness of the need to maintain the ability to masticate a variety of foods throughout the individual's lifetime in order to provide for his nutritional, bulk and fiber needs has generated an expanding market for dentures. Over the years a host of different devices and a number of various methods of making them from synthetic materials have been utilized.

During the early portion of this century the use of plastic resins in denture devices was introduced. The resins were found to provide a more natural appearance than heretofore obtainable from prior materials. Also, materials of increased density and low porosity markedly reduced any health hazards associated with dentures. To this end, the denture industry after extensive testing and evaluation has adapted the plastic resin methyl methacrylate or, acrylic as it is commonly referred to, as the favored synthetic material for custom dentures. This material has remained the favored synthetic material for the fabrication of dentures to this date.

The characteristic of synthetic materials that enables them to be shaped and formed prior to the curing process which sets the material into a permanent form renders plastics or resins well suited for use in the dental laboratory. At present, conventional practice in the manufacture of individually tailored dentures begins with the dentist taking impressions of the oral cavity of the individual being fitted. A subsequent cast wax model is made in a dental laboratory to provide a working model for the technician.

The laboratory technician sets artificial teeth in both the upper and lower wax modules. At this time, both modules are usually mounted in a jig to allow review and adjustment of the occlusal aspects of the dentures. When the laboratory technician is satisfied as to the conformance of the module with the cast impression, the overall appearance of the denture and the provision of a satisfactory occlusal orientation of the teeth, the assemblage is then delivered to the dentist for custom fitting to the patient. After the fit is adjusted by the dentist, the wax model is returned to the laboratory for use in the preparation of an investment casting wherein dental stone or the like is placed around the wax model. The wax is melted to provide a cavity into which the acrylic is placed. After curing, the hardened or fixed denture is returned to the dentist whereupon the fit is again reviewed and often modified by the removal or addition of acrylic material.

The recipient's dentist then completes the fitting of his patient by trimming or adding material or modifying the size, shape and orientation of the denture to the individual's oral cavity. The dentist is working at this time with a fully cured synthetic material denture with mechanical techniques, such as grinding, to provide the details and adjustments necessary to provide a proper fit of the custom denture. This is an expensive and time consuming process requiring highly skilled personnel and thus is prohibitively expensive for the large portion of the population desirous of obtaining the benefits of denture devices.

To overcome the difficulties in trying to obtain custom dentures through the previously noted method, a combination of techniques have been employed. In one method, a fully cured module of synthetic material is made with the teeth permanently secured therein. Deformable backing or liner layers of uncured materials are provided against the cured material. The layered combination is then impression fitted in the patient's mouth for adjustment to the dimensions of the palatal vault. However, the fully cured module does not provide the dentist with the ability to modify the lateral spacing between the posterior teeth to accommodate different shapes and spacings for the endentulus ridge. Thus, only a partial customization is possible with this approach.

Other proposals for providing a custom denture device from a preformed module have included providing an embedded wire structure in an elastomeric environment as part of the cured denture device. The wire portion is deformed to simulate the approximate contours of the patient's palatal region. This approach is a compromise between fit and cost in that the denture can only be shaped to accommodate the large contours of the palatal vault and not the contours of the ridged portion of the oral cavity thus resulting in substantial discomfort to the user.

Accordingly, the present invention is directed to an uncured denture module formed to standard dimensions and which is capable of being conformed by the dentist to both the edentulus ridge and palatal areas of the oral cavity. The occlusal aspects of the dentures can be reviewed by the dentist prior to curing and the module then cured to permanently fix the teeth in the dentist's office. The invention provides a method of making custom dentures during a single visit to the dentist thereby reducing the costs thereof and the need for a series of steps performed at different locations.

SUMMARY OF THE INVENTION

This invention is directed to a method of making a custom denture from a representation of an individual's oral cavity, typically a cast impression of the edentulus ridge regions and the palatal contours.

The dentist generates the cast impression in the generally accepted manner and utilizes this impression to conform thereto a denture module of uncured synthetic material preformed to generalized dimensions. The module including the tooth sockets and surrounding detail is prepared elsewhere of acrylic material in a pressure molding technique to standardized dimensions corresponding to a typical oral cavity for a significant portion of the population. In the practice of this method, the module as molded contains recesses therein adapted to receive artificial teeth. Normally, the module is provided with an array of teeth, removably placed in the sockets and cooled to maintain the material in an uncured state.

The uncured module is shipped to and stored by the dentist at a low temperature until used. At the time of usage, the dentist has made a conventional cast impression of the oral cavity and the module is withdrawn from storage. The cast impression is heated and the module placed thereon and urged into conformance with the surface of the cast impression. The artificial teeth located in the recesses of the uncured conformed module may be adjusted, respositioned or replaced to provide a desired appearance and bite. The preparation of both the maxillary and mandibular dentures simultaneously permits the modules to be placed on a jig or other fixture to visually review the occlusal aspects of the denture at any stage in the process.

The uncured module containing the artificial teeth and conformed to and positioned on the cast impression is then placed in a vessel or flask. Next, it is provided with a protective coating and heated, typically by immersion in heated water, to effect curing. After curing has taken place, the assemblage is removed and the coating material placed thereon is stripped to provide the custom denture.

By prefabricating the module and recesses to standard dimensions only, a limited inventory of sizes is required to be stored by the dentist. As stored, the modules are provided with the artificial teeth in the recesses. The placement of teeth occurs prior to lowering the temperature of the assembly thereby reducing any deformation of the recesses during handling and eliminating the effects of shrinkage due to the reduction in temperature. Since the artificial teeth do not extend through the module, the subsequent step of conforming the opposing surface of the module to the heated cast impression may be readily conducted without substantial alteration of the relative positions of individual teeth. However, large adjustments to accommodate a typical palatal vaults and ridges can be readily made due to the fact that the module is uncured at this time. To reduce the effect of the step of conforming upon the alignment of the teeth, a prior step of interconnecting individual teeth to provide dimensional stability can be utilized if desired.

Further features and advantages of the invention will become more readily apparent from the following detailed description of specific embodiments of the invention when taken in conjunction with the accompanying drawings.

BRIEF DESCRIPTION OF THE DRAWINGS

FIG. 7 is an exploded view in perspective with a partial fixed array plus a number of individual artificial teeth for placement in the tooth sockets of a maxillary module.

FIG. 8 is an exploded view in perspective of one type of complete fixed array of artificial teeth for placement in the recess of a maxillary module.

FIG. 9 is a perspective view of a second type of complete fixed array of artificial teeth for placement in a module.

FIG. 10 is a maxillary module with artificial teeth placed therein and including means for maintaining the occlusal aspect thereof.

FIG. 11 is a partial side view in section of the embodiment of FIG. 10.

DESCRIPTION OF THE PREFERRED EMBODIMENTS

Figure 1:
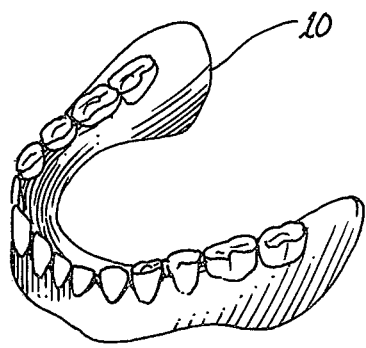
FIGS. 1 and 2 show the mandibulary and maxillary dentures respectively produced by the present invention.
Figure 2:
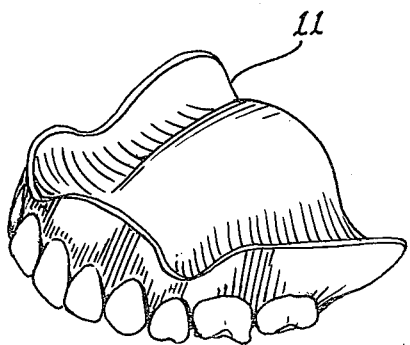

Referring now to FIGS. 1 and 2, the mandibulary and maxillary dentures 10 and 11 respectively formed in accordance with the present invention are shown. Each denture includes a number of artificial teeth fixedly mounted in a cured synthetic material base which has been conformed to the contours and dimensions of both the endentulus ridge and palatal vault of the individual user. While the base material utilized in connection with this invention may be any approved synthetic resin or plastic, the dental acrylic, methyl methacrylate, is today the dominant material used in the manufacture of denture devices. Since the present invention is utilized for making both the maxillary and mandibular units with the difference being only one of mold design, the following description is directed to the process of making different maxillary embodiments. It being understood that the teaching applies to the method of making many different forms of denture devices, both complete and partial incorporating artificial teeth in a synthetic resin or plastic base.

Figure 3:
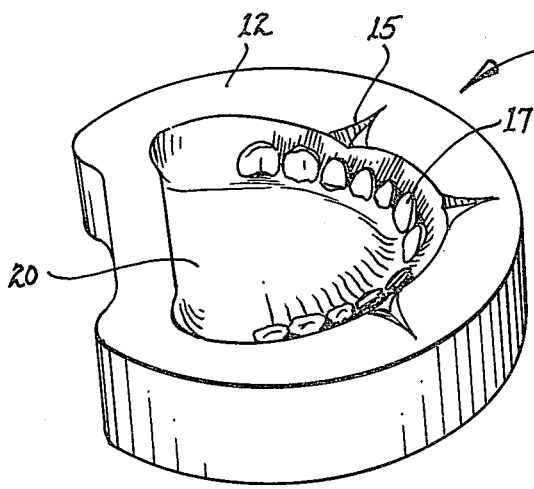
FIGS. 3 and 4 show the lower and upper halves respectively of a mold utilized in the formation of a module in accordance with the present invention.
Figure 4:
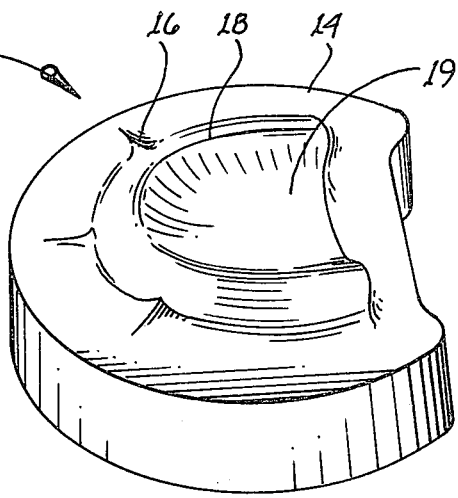

The present invention includes the initial making of a detailed dental module of uncured synthetic material in a relatively high pressure mold. The top and bottom halves of the mold, shown in FIGS. 3 and 4 respectively, are preferably formed of a synthetic material, such as monothane, a commercially available single component polyurethane material.

The upper half of the mold 14 includes an arcuate raised portion 18 which generally comprises the outline of an endentulus ridge. Located in the segment within the arc is a depression 19 corresponding to a palatal vault. The lower half of the mold 12 includes a plurality of simulated bases of teeth 17 protruding therefrom along with the detailing or festooning which enhances the aesthetic appearance of a denture. These protrusions are designed to form the recesses or tooth sockets for artificial teeth. Also, a raised portion 20 is centrally located therein in general conformance with palatal region of the other half of the mold. Relief regions 15, 16 are normally provided in each half of the mold to permit the migration of excess material thereto when the halves are assembled and subjected to pressure.

In operation, the mold is provided with a measured amount of acrylic resin placed therein. The halves are assembled, registered and inserted in a hydraulic press which subjects them to a relatively high pressure in the range of 3,000 to 5,000 psi to insure the formation of a low porosity module. Since the artificial teeth are not within the mold, high pressures can be utilized in the present process without encountering the problem of flashing overlying and adhering thereto. It is to be noted that the particular synthetic material employed dictates the pressure and time required to mold the article. In the practice of the present invention, the 3,000 psi figure has been found to provide highly satisfactory results when used with the ADA approved type #139 standard acrylic resin available from the Eschem Co.

The molding process is accomplished without the addition of external heat. As a result, the molded material remains in an uncured state. To that end, the unparted mold halves are placed in a cooling environment, normally below 32° F., to impart rigidity thereto and to prevent undesired curing effects from being initiated. In a preferred sequence, the unparted mold is placed under refrigeration at a temperature of 10 degrees F. for a period of 24 hours to insure that the denture remains uncured. Prior to shipment to the dentist, the molds are disassembled. The cooled denture module having the general dimensions of the mold and including the tooth sockets is removed and placed on a contoured carrier. In operation, the carrier is formed from an expanded plastic.

Figure 5:
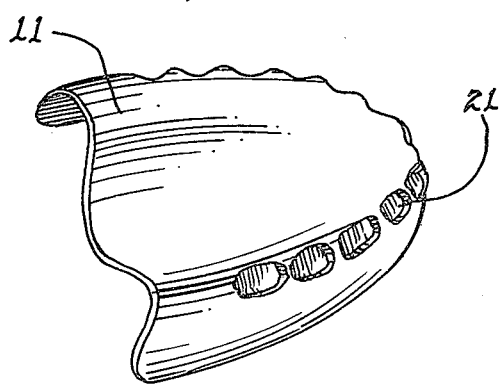
FIG. 5 is a perspective view of a maxillary module made in accordance with the invention.
Figure 6:
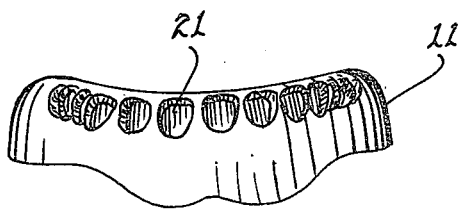
FIG. 6 is a front view of the module shown in FIG. 5.

A maxillary module removed from the mold is shown in the perspective view of FIG. 5 and the frontal view of FIG. 6 wherein the details of the tooth sockets formed in the exposed surfaces are shown. It is to be noted that the inner surface of the module; that surface which is intended to be conformed to and rest against the endentulus ridge and palatal surface of the user is unbroken. This surface is that formed and shaped by the top half 14 of the mold shown in FIG. 4. The maxillary module of FIGS. 5 and 6 is shown rotated 180 degrees from the position it occupies in the oral cavity of the user. However, the orientation shown corresponds to its position when placed on the carrier for further work.

While the module on its carrier is still in a rigid state due to its lowered temperature, an array of prosthetic or artificial teeth are placed therein by an assembler. The structural rigidity of the module prevents any significant deformation of the modules and loss of detail surrounding the recesses. At this time, the prosthetic teeth are not securely anchored in the recesses and do not become so until the finally curing step of the process. This provides the fitting dental practitioner with the latitude to replace teeth for aesthetic or other reasons at the time of fitting.

In practice, good results have been obtained by an initial prolonged cooling, typically 24 hours, of the module prior to the placement of the teeth therein. Thus, relatively unskilled personnel can handle the placement of the prosthetic teeth without damaging the module. When the prosthetic teeth are in place, the module is returned to the refrigerated storage and placed on the carrier to await shipment. As an alternative, the mold containing the module can be initially chilled to a temperature well below ambient but which need not be as low as 10° F. Then the module is removed, teeth installed and the device and its carrier further cooled in a low temperature storage container. This alternative does not require the low temperature cooling of the mold mass and the subsequent recooling of the module to the low storage temperature.

Reference has been made to the placement of an array of prosthetic teeth in the module of uncured resin prior to shipment. This array of teeth may include either individual prosthetic teeth, a preformed assemblage thereof or a combination of the two approaches. To utilize the versatility of the present invention which provides the dentist with the ability to modify the asthetic appearance as well as the fit in the dental office, the formation of a module having recesses for each individual tooth as shown in FIGS. 5 and 6 is recommended. Upon receipt of a module containing individual teeth, the dentist can if necessary alter individual tooth orientation. This is especially advantageous in situations wherein only a partial or one denture plate is being made for the patient.

The modules of FIGS. 7 and 8 show alternative approaches which reduce the labor component of denture cost by incorporating partial and complete preformed arrays of teeth. In particular, FIG. 7 shows the combination of a partial preformed array with a number of individual prosthetic teeth 24 fixedly embedded in a fully detailed and cured base 23. The preformed array is preferably made of the same synthetic material utilized in forming module 11. As shown, the module 11 contains a plurality of recesses 21 for receiving individual teeth 22 along with an extended impression 25 to accommodate the base 23 of the fixed array. In FIG. 8, the module 11 is molded with a single recess extending along the exposed surface of the endentulus ridge for receiving an integral or segmented fixed array 31 of prosthetic teeth. Array 31, as shown, does not contain a synthetic material base since the teeth are either maintained in fixed relationship by a wire extending internally therethrough or by forming the array initially as an integral unit, for example by injection molding. To provide the dentist with an increased ability to shape the module for a custom fit, the array 31 can be made in three adjacent segments. This permits the dentist to alter the shape of the endentulus ridge to suit the patient. The integral array prevents lateral adjustment of the anterior portion of the ridge.

Another type of complete fixed array 32 of prosthetic teeth suited for placement in the dental module is shown in FIG. 9 wherein the individual teeth 34 are fixedly secured in a detailed base 33 of fully cured acrylic. This fixed array fashioned by conventional techniques and referred to as a U-shaped stringer is commercially available at present.

In the practice of the present method wherein individual artificial teeth are inserted in the uncured module prior to shipment, it is desirable to provide a means for maintaining the relative positions of the teeth along with the occlusal aspect thereof. Subsequent handling especially during conformance of the module with a cast impression of the individual's oral cavity and any trial placement in the patient's mouth is likely to cause movement of the teeth and the loss of the necessary close fit between tooth and socket. In order to minimize the possibility of this occurrence, a removable containment layer 35, shown in FIGS. 10 and 11, is formed about the individual teeth 36 of uncured module 11. Good results have been obtained with a low melting point wax poured into an intermediate mold which receives the teeth in an inverted position. The intermediate mold is placed on the teeth after they are in place in the module, then the assembly is inverted and the wax is poured. The intermediate mold has a series of recesses therein which maintain the relative spacing of the teeth as the wax is poured and permit the ends of the teeth 36 to protrude slightly, for example one-eighth of an inch, therefrom. The fact that the edges of the teeth protrude enables the occlusal aspects of maxillary and mandibulary modules to be reviewed in a fixture or jig during the subsequent conformance to the cost impression in the dentist's office.

Figure 14A:
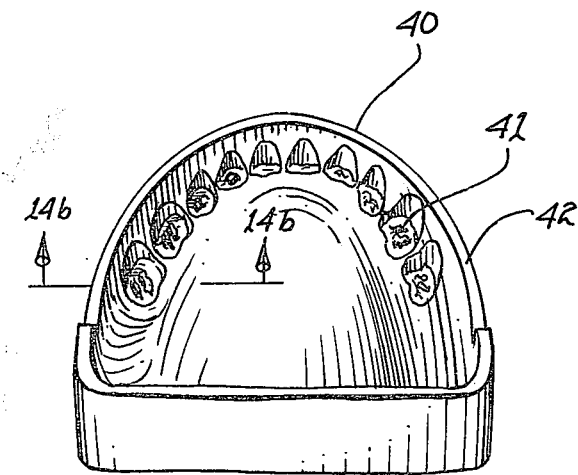
FIGS. 14a and b show top view of a fixture used in fabricating an array of individual teeth therein and a partial section thereof.
Figure 14B:
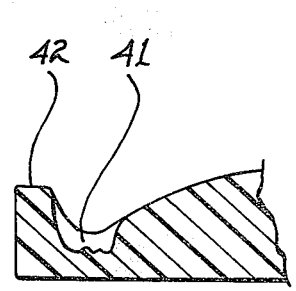
Figure 15:
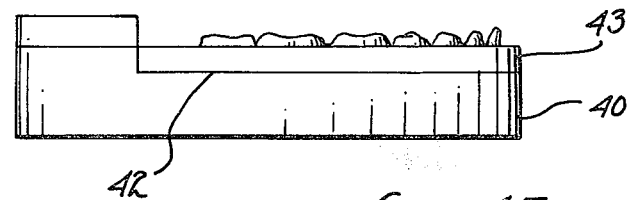
FIG. 15 is a side view of the fixture of FIG. 14.

An alternative to the use of a poured containment means is shown in FIGS. 14a and b, 15 and 16 wherein a fixture 40 is provided with a plurality of tooth sockets 41 spaced to receive the individual artificial teeth. The alignment and spacing of the teeth sockets for each fixture is in exact agreement with the corresponding mold.

The assembler places the individual artificial teeth sequentially in the receiving sockets 41. A cut-out region 42 is provided in the peripheral portion of fixture 40 to be adjacent each installed tooth. In addition, the cut-out region 42 above is the lower extremity of each tooth so that the insertion of curved retaining strip 43 in the cut-out region does not contact the root structure of the teeth. Also, the height of retaining strip 43 is made to be less than the height of the smallest tooth in the array thereby insuring that each tooth protrudes thereabove.

Figure 16:
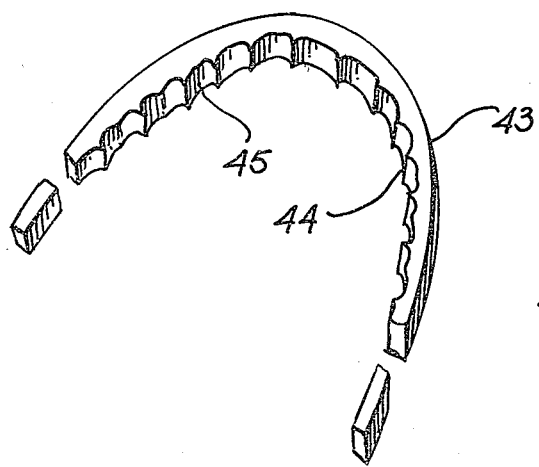
FIG. 16 is a top view of the retaining means used in the fixture of FIG. 15.

Strip 43 is formed with receiving curves 44 which are in agreement with the master mold and therefore alignment with the sockets of fixture 40. A thin layer 45 of adhesive material is provided on the inner surface of strip 43 as shown in FIG. 16 to contact the individual teeth. When the teeth are properly located, the assembler places the strip 43 against the teeth they adhere thereto and are removed as a unit for placement in the module. The strip adhering to the surface of the teeth in the intermediate position serves as the means for maintaining the relative positions of the teeth during subsequent processing.

Figure 12:
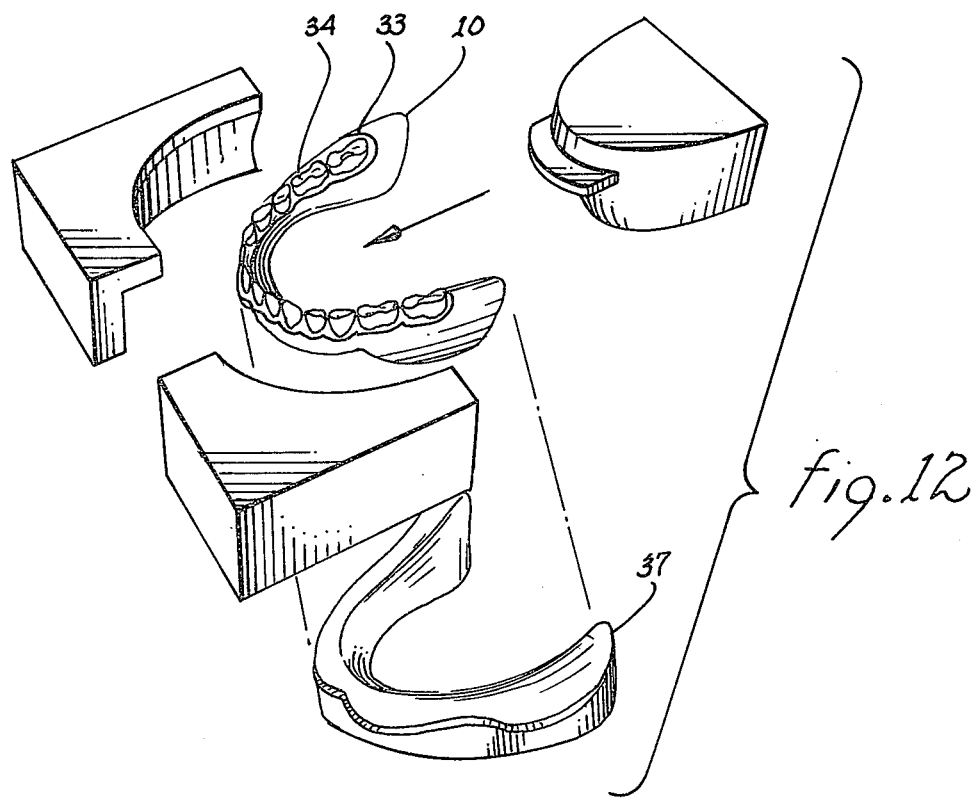
FIGS. 12 and 13 show the modules, carrier and protective means thereof.
Figure 13:
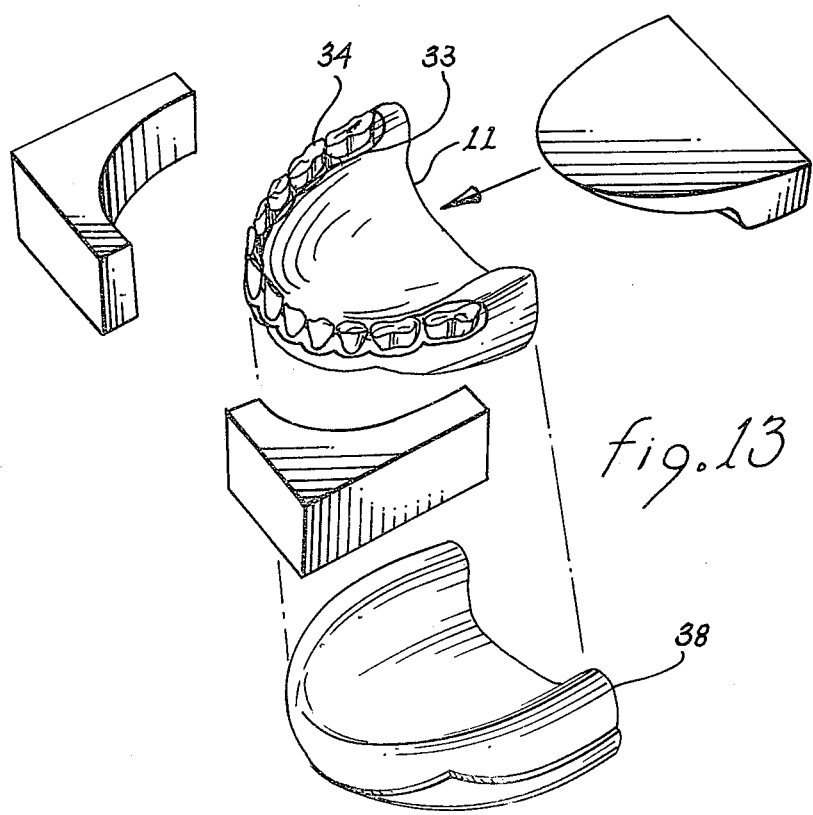

FIGS. 12 and 13 show the carriers 37 and 38 for the mandibulary and maxillary modules respectively. As previously mentioned, each module is placed on a carrier for the placement of the teeth therein and low temperature storage. Each carrier is also a part of a split mold assembly for shipment to the dentist's office and storage in the refrigerator. The split mold for each module includes four parts, one of which is the carrier, and they differ only in providing for the palatal region of module 11. For transport, the modules are typically vacuum packed to reduce any curing effects in the interim period and shipped in an insulated container.

At the time the patient is being fitted for dentures, a cast impression is made by the dentist to provide a representation of the patient's oral cavity. Any approved series of materials can be utilized in this well-known technique. The dentist has an inventory normally three modules of different standardized dimensions. The dentist selects the appropriate generalized size for use in the practice of the present method. Then, the cast impression is heated to a temperature above ambient, usually by the use of heated tap water, and the uncured module with the artificial teeth in place is located thereon. By conduction from the heated impression, the adjacent region of the module rises in temperature and softens thereby permitting conformance to the contours of the cast impression. The dentist urges the module into agreement with the ridge and palatal contours of the impression. The occlusal aspects of the prosthetic teeth are maintained constant during conformance unless intentionally altered by the dentist. The alignment can be readily checked in a conventional fixture prior to subsequent curing, if desired.

In the event that the patient's palatal vault or ridge structure is substantially out of line with the generalized dimension used in the fabrication of the uncured module, the palatal area can be notched and additional uncured acrylic material can be provided in the notch. Similarily material can be removed from the module, if found necessary. The module is then replaced on the cast impression and conformance therewith obtained. Any material so used is preferably the same material as in the module to insure that they merge into an integral structure during the subsequent curing.

After conformance and a review of the occlusal aspects, the module is then cured in a heated water reservoir. Typically, the water temperature is about 212° F. and immersion for thirty minutes accomplishes the curing of the synthetic material. The immersion can utilize a conventional dental flask into which the impression and module are placed and covered with a protective coating, typically a dental plaster. After curing, the combination is removed from the dental flask and the protective material removed and the surfaces lightly polished. The custom denture is then ready for immediate usage.

The overall or gross dimensions of the human oral cavity do vary greatly throughout the bulk of the population. However, the ability to conform the module in the present process requires that only a limited number, typically three, of different size uncured dental modules be inventoried by the dentist. The versatility of the present method and module permit the adjustment of the present device to the individual's particular oral cavity dimensions and configuration. This adjustment can be made in a short period of time during a single visit to the dental office. Thus, a custom device is provided in a single visit.

While the above description has referred to specific embodiments of the invention, it is to be noted that many modifications and variations may be made therein without department from the scope of the invention as claimed.

I claim:
1. In a method of making a custom denture from a representation of an oral cavity, the steps comprising:
    (a) preparing a denture module of uncured synthetic material containing at least one recess therein adapted to receive an array of prosthetic teeth;
    (b) maintaining the material of said module in an uncured state;
    (c) placing prosthetic teeth in said module;
    (d) placing said module on the representation of the oral cavity;
    (e) conforming said module to the surface contours of said representation; and
    (f) curing the conformed module and teeth therein to form a custom denture.
2. The method of claim 1 wherein the step of maintaining the module in an uncured state includes the step of cooling said module to a temperature lower than the ambient temperature.
3. The method of claim 2 further comprising the step of heating the representation of the oral cavity to a temperature higher than the ambient temperature prior to placing the module thereon.
4. The method of claim 3 wherein the step of curing the conformed module and teeth includes the steps of confining said module, teeth and representation in a container and applying heat thereto in order to effect curing thereof.
5. The method of claim 4 wherein the step of preparing the denture module includes the step of forming a module of standard dimensions in a pressure mold.
6. The method of claim 5 wherein the step of placing the artificial teeth in said module includes the step of interconnecting individual artificial teeth to provide stability therefor.
7. The method of claim 6 wherein the step of interconnecting the teeth includes providing the array of artificial teeth with removable means for maintaining the occlusal aspects thereof during subsequent processing.

8. The method of claim 7 wherein the step of cooling said module comprises the step of lowering the temperature of said module to at least 32° F.

9. The method of claim 7 further comprising the step of again cooling said module after placing the teeth therein.

10. The method of claim 7 further comprising the step of placing said cooled module and teeth on a carrier mold for storage.

11. The method of claim 10 further comprising the step of applying a removable coating to the conformed module prior to curing said module.

12. The method of claim 11 wherein the step of curing said conformed module includes heating said module to substantially 212° F. and maintaining the module at said elevated temperature for an extended period.

13. The method of claim 12 further comprising the step of removing said coating after curing said conformed module.

14. The method of claim 1 wherein the step of conforming the module includes the modifying the amount of the uncured material in said module to thereby aid in conforming said module to the configuration of said representation.

15. The method of claim 14 further comprising the step of making of a rigid cast model from an impression of the oral cavity of the individual which includes the ridge and palatal contours thereof.

16. The method of claim 15 further comprising the steps of: (a) mounting artificial teeth in a base of synthetic material; and (b) curing said synthetic material prior to placing the artificial teeth in said module.

17. The method of claim 16 wherein the step of mounting said artificial teeth includes mounting said teeth in the same synthetic material utilized in preparing said module.

* * * * *